US007567353B2

(12) United States Patent
Bischoff et al.

(10) Patent No.: US 7,567,353 B2
(45) Date of Patent: Jul. 28, 2009

(54) AUTOMATED PROCESS CONTROL USING OPTICAL METROLOGY AND PHOTORESIST PARAMETERS

(75) Inventors: Joerg Bischoff, Illmenau (DE); David Hetzer, Dresden (DE); Manuel Madriaga, San Jose, CA (US)

(73) Assignee: Tokyo Electron Limited, Tokyo (JP)

( * ) Notice: Subject to any disclaimer, the term of this patent is extended or adjusted under 35 U.S.C. 154(b) by 300 days.

(21) Appl. No.: 11/729,700

(22) Filed: Mar. 28, 2007

(65) Prior Publication Data

US 2008/0241975 A1    Oct. 2, 2008

(51) Int. Cl.
*G01B 11/04* (2006.01)
(52) U.S. Cl. .................... 356/636; 356/601; 356/237.5
(58) Field of Classification Search ... 356/237.1–237.5, 356/601, 625, 636
See application file for complete search history.

(56) References Cited

U.S. PATENT DOCUMENTS

| 5,347,356 | A | 9/1994 | Ota et al. |
| 5,468,580 | A | 11/1995 | Tanaka |
| 5,926,690 | A | 7/1999 | Toprac et al. |
| 6,304,999 | B1 | 10/2001 | Toprac et al. |
| 6,383,824 | B1 | 5/2002 | Lensing |
| 6,383,888 | B1 | 5/2002 | Stirton |
| 6,433,871 | B1 | 8/2002 | Lensing et al. |
| 6,451,621 | B1 | 9/2002 | Rangarajan et al. |
| 6,597,463 | B1 | 7/2003 | Singh et al. |
| 6,609,086 | B1 | 8/2003 | Bao et al. |
| 6,625,512 | B1 | 9/2003 | Goodwin |
| 6,633,831 | B2 | 10/2003 | Nikoonahad et al. |

(Continued)

FOREIGN PATENT DOCUMENTS

GB    2417420 A    3/2006

OTHER PUBLICATIONS

Braun, A. E. (May 1, 2002). "Thin-Film Measurement Enters New Frontiers," *Semiconductor International*, located at <http://www.semiconductor.net/article/CA213802.html> visited on Jun. 12, 2008. (7 pages).

(Continued)

*Primary Examiner*—Hoa Q Pham

(57) ABSTRACT

To control a photolithography cluster using optical metrology, a structure is fabricated on a wafer using the photolithography cluster. A measured diffraction signal off the structure is obtained. The measured diffraction signal is compared to a simulated diffraction signal. The simulated diffraction signal is associated with one or more values of one or more photoresist parameters. The one or more photoresist parameters characterize behavior of photoresist when the photoresist undergoes processing steps in the photolithography cluster. The simulated diffraction signal was generated using one or more values of one or more profile parameters. The one or more values of the one or more profile parameters used to generate the simulated diffraction signal were derived from the one or more values of the one or more photoresist parameters associated with the simulated diffraction signal. If the measured diffraction signal and the simulated diffraction signal match, then one or more values of one or more photoresist parameters used in the photolithography cluster are determined to be the one or more values of the one or more photoresist parameters associated with the matching simulated diffraction signal. One or more process parameters or equipment settings of the photolithography cluster are adjusted based on the one or more values of the one or more photoresist parameters.

24 Claims, 13 Drawing Sheets

U.S. PATENT DOCUMENTS

| | | | |
|---|---|---|---|
| 6,643,557 | B1 | 11/2003 | Miller et al. |
| 6,657,736 | B1 | 12/2003 | Finarov et al. |
| 6,701,206 | B1 | 3/2004 | Markle et al. |
| 6,708,075 | B2 | 3/2004 | Sonderman et al. |
| 6,756,243 | B2 | 6/2004 | Pasadyn et al. |
| 6,772,084 | B2 | 8/2004 | Bischoff et al. |
| 6,782,337 | B2 | 8/2004 | Wack et al. |
| 6,785,638 | B2 | 8/2004 | Niu et al. |
| 6,791,679 | B2 | 9/2004 | Engelhard et al. |
| 6,891,626 | B2 | 5/2005 | Niu et al. |
| 6,895,295 | B1 | 5/2005 | Grover et al. |
| 6,943,900 | B2 | 9/2005 | Niu et al. |
| 6,999,254 | B1 | 2/2006 | Phan et al. |
| 7,042,569 | B2 | 5/2006 | Sezginer et al. |
| 7,043,397 | B2 | 5/2006 | Johnson |
| 7,065,423 | B2 | 6/2006 | Prager et al. |
| 7,072,049 | B2 | 7/2006 | Niu et al. |
| 7,092,110 | B2 | 8/2006 | Balasubramanian et al. |
| 7,126,700 | B2 | 10/2006 | Bao et al. |
| 7,158,896 | B1 | 1/2007 | Singh et al. |
| 7,171,284 | B2 | 1/2007 | Vuong et al. |
| 7,186,650 | B1 | 3/2007 | Dakshina-Murthy |
| 7,224,456 | B1 | 5/2007 | Phan et al. |
| 7,224,471 | B2 | 5/2007 | Bischoff et al. |
| 7,280,230 | B2 | 10/2007 | Shchegrov et al. |
| 7,372,583 | B1 * | 5/2008 | Jin et al. ............ 356/625 |
| 7,417,750 | B2 * | 8/2008 | Vuong et al. ......... 356/636 |
| 2004/0017574 | A1 | 1/2004 | Vuong et al. |
| 2004/0267397 | A1 | 12/2004 | Doddi et al. |
| 2005/0209816 | A1 | 9/2005 | Vuong et al. |
| 2007/0185684 | A1 | 8/2007 | Vuong et al. |
| 2008/0007739 | A1 | 1/2008 | Vuong et al. |
| 2008/0170241 | A1 * | 7/2008 | Chard et al. ......... 356/625 |
| 2008/0243730 | A1 * | 10/2008 | Bischoff et al. ....... 706/12 |
| 2008/0249754 | A1 * | 10/2008 | Niu et al. ............ 703/6 |
| 2009/0063075 | A1 * | 3/2009 | Liu et al. ............ 702/82 |
| 2009/0063076 | A1 * | 3/2009 | Liu et al. ............ 702/82 |
| 2009/0063077 | A1 * | 3/2009 | Liu et al. ............ 702/82 |

OTHER PUBLICATIONS

MacCormack, S. et al. (Feb. 15, 1997). "Powerful, Diffraction-Limited Semiconductor Laser Using Photorefractive Beam Coupling," *Optics Letters* 22(4):227-229.

McNeil, J. R. (2000). "Scatterometry Applied to Microelectronics Processing," *IEEE*, pp. 37-38.

Adler, C. L. et al. (Jun. 1997). "High-Order Interior Caustics Produced in Scattering of a Diagonally Incident Plane Wave by a Circular Cylinder," *Journal of the Optical Society of America A* 14(6):1305-1315.

Arthur, G. G. (Jul. 1997). "Enhancing the Development-Rate Model for Optimum Simulation Capability in the Subhalf-Micron Regime," *Proceedings of SPIE* 3049:189-200.

Ausschnitt, C. P. (Feb. 23, 2004). "A New Approach to Pattern Metrology," *Proceedings of SPIE* 5375:51-65.

Benincasa, D. S. et al. P. (Apr. 1987). "Spatial Distribution of the Internal and Near-Field Intensities of Large Cylindrical and Spherical Scatterers," *Applied Optics* 26(7):1348-1356.

Haykin, S. (1999). *Neural Networks*. 2nd edition, M. Horton ed., Prentice Hall: Upper Saddle River, New Jersey, 9 pages (Table of Contents).

Ilkayev, D. R. et al. (Autumn 1994). "Predicting Positive Photoresist Post Exposure Bake Effects: Comparison of Simulation Methods," *Microlithography World*, pp. 17-20.

Keeman, C. (2005). "Support Vector Machine—An Introduction" *In Support Vector Machines: Theory and Applications*. Wang, L. ed., Springer-Verlag Berlin Heidelberg: The Netherlands, pp. 1-47.

Levinson, H.J. (2001). *Principles of Lithography*. SPIE Press: Bellingham, Washington, Chapter 4.3-4.7, pp. 109-132.

Levinson, H. J. (2001). "Photoresists" Chapter 3 *In Principles of Lithography*. SPIE Press: Bellingham, Washington, pp. 55-96.

Li, L. (1996). "Formulation and comparison of two recursive matrix algorithms for modeling layered diffraction gratings," *Journal of the Optical Society of America A* 13:1024-1035.

Lock, J. A. et al. (Oct. 2000). "Exterior Caustics Produced in Scattering of a Diagonally Incident Plane Wave by a Circular Cylinder: Semiclassical Scattering Theory Analysis," *Journal of the Optical Society of America A* 17(10):1846-1856.

Mack, C. A. (Autumn 1994). "Photoresist Development," *Microlithography World*, pp. 22-24.

Mack, C. A. (Feb. 2002). "Using the Normalized Image Log-Slope Part 5: Development," *Microlithography World*, pp. 18, 26.

Mack, C. A. (Spring 1999). "Absorption and Reflectivity: Designing the Right Photoresist," *Microlithography World*, pp. 20-21.

Mack, C. A. (Summer 1997). "Antireflective Coatings," *Microlithography World*, pp. 29-30.

Mack, C. A. (Winter 1994). "Positive Photoresists—Exposure," *Microlithography World*, pp. 21-23.

Mack, C. A. (Winter 1995). "Photoresist Development (Cont.)," *Microlithography World*, pp. 24-26.

Owen, J. F. et al. (Nov. 1981). "Internal Electric Field Distributions of a Dielectric Cylinder at Resonance Wavelengths," *Optics Letters* 6(11):540-542.

Platt, J. C. (1999). "Fast Timing of Support Vector Machine Using Sequential Minimal Optimization" Chapter 12 *In Advances in Kernal Methods: Support Vector Learning*. Schölkopf et al. eds., MIT Press: Cambridge, MA, pp. 185-208.

Reichmanis, E. et al. (Nov./Dec. 1992). "Chemically Amplified Resists for Deep-UV Lithography: A New Processing Paradigm," *Microlithography World*, pp. 7-14.

U.S. Appl. No. 11/371,752, filed Mar. 8, 2006 for Vuong et al.
U.S. Appl. No. 11/484,484, filed Jul. 10, 2006 for Madriaga et al.
U.S. Appl. No. 11/594,659, filed Nov. 7, 2006 for Vuong et al.
U.S. Appl. No. 11/726,076, filed Mar. 20, 2007 for Vuong et al.
U.S. Appl. No. 11/729,497, filed Mar. 28, 2007 for Bischoff et al.
U.S. Appl. No. 11/729,498, filed Mar. 28, 2007 for Bischoff et al.
U.S. Appl. No. 11/787,025, filed Apr. 12, 2007 for Jin et al.

Xu. Y. (Jul. 1995). "Electromagnetic Scattering by an Aggregate of Spheres," *Applied Optics* 34(21):4573-4588.

* cited by examiner

AUTOMATED PROCESS CONTROL USING OPTICAL METROLOGY AND PHOTORESIST PARAMETERS

BACKGROUND

1. Field

The present application generally relates to optical metrology of a structure formed on a semiconductor wafer, and, more particularly, to automated process control using optical metrology and photoresist parameters.

2. Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured diffraction signal) is compared to a library of simulated diffraction signals. Each simulated diffraction signal in the library is associated with a hypothetical profile. When a match is made between the measured-diffraction signal and one of the simulated diffraction signals in the library, the hypothetical profile associated with the simulated diffraction signal is presumed to represent the actual profile of the periodic grating.

The library of simulated diffraction signals can be generated using a rigorous method, such as rigorous coupled wave analysis (RCWA). More particularly, in the diffraction modeling technique, a simulated diffraction signal is calculated based, in part, on solving Maxwell's equations. Calculating the simulated diffraction signal involves performing a large number of complex calculations, which can be time consuming and costly.

SUMMARY

In one exemplary embodiment, to control a photolithography cluster using optical metrology, a structure is fabricated on a wafer using the photolithography cluster. A measured diffraction signal off the structure is obtained. The measured diffraction signal is compared to a simulated diffraction signal. The simulated diffraction signal is associated with one or more values of one or more photoresist parameters. The one or more photoresist parameters characterize behavior of photoresist when the photoresist undergoes processing steps in the photolithography cluster. The simulated diffraction signal was generated using one or more values of one or more profile parameters. The one or more values of the one or more profile parameters used to generate the simulated diffraction signal were derived from the one or more values of the one or more photoresist parameters associated with the simulated diffraction signal. If the measured diffraction signal and the simulated diffraction signal match, then one or more values of one or more photoresist parameters used in the photolithography cluster are determined to be the one or more values of the one or more photoresist parameters associated with the matching simulated diffraction signal. One or more process parameters or equipment settings of the photolithography cluster are adjusted based on the one or more values of the one or more photoresist parameters.

DETAILED DESCRIPTION OF EXEMPLARY EMBODIMENT(S)

In order to facilitate the description of the present invention, a semiconductor wafer may be utilized to illustrate an application of the concept. The methods and processes equally apply to other work pieces that have repeating structures. Furthermore, in this application, the term structure when it is not qualified refers to a patterned structure.

Figure 1A:
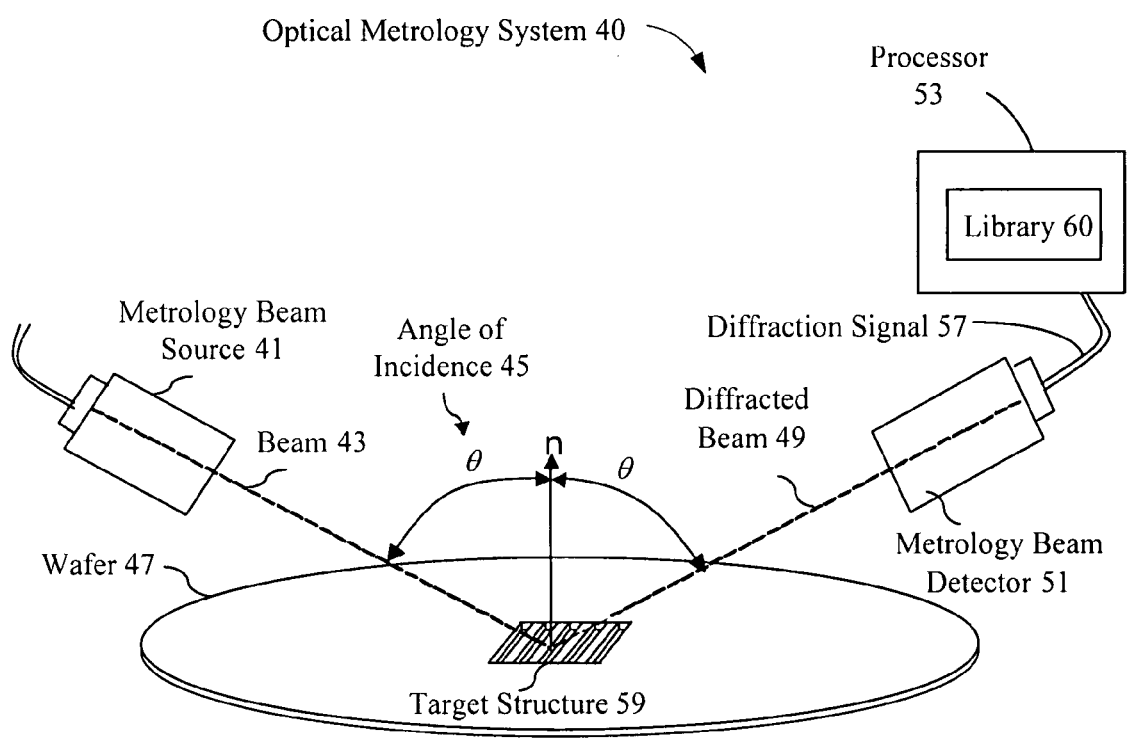
FIG. 1A is an architectural diagram illustrating an exemplary embodiment where optical metrology can be utilized to determine the profiles of structures on a semiconductor wafer.

FIG. 1A is an architectural diagram illustrating an exemplary embodiment where optical metrology can be utilized to determine the profiles of structures on a semiconductor wafer. The optical metrology system 40 includes a metrology beam source 41 projecting a beam 43 at the target structure 59 of a wafer 47. The metrology beam 43 is projected at an incidence angle θ towards the target structure 59. A diffraction beam 49 is measured by a metrology beam detector 51. A diffraction signal 57 is transmitted to a processor 53. The processor 53 compares the measured diffraction signal 57 against a library 60 of simulated diffraction signals. In one exemplary embodiment, the library 60 instance best matching the measured diffraction signal 57 is selected. An optical metrology system is described in U.S. Pat. No. 6,913,900, entitled GENERATION OF A LIBRARY OF PERIODIC GRATING DIFFRACTION SIGNAL, by Niu, et al., issued on Sep. 13, 2005, and is incorporated in its entirety herein by reference. Other exemplary optical metrology systems that do not use libraries can be used.

The library of simulated diffraction signals can be generated using a machine learning system (MLS). Prior to generating the library of simulated diffraction signals, the MLS is trained using known input and output data. In one exemplary embodiment, simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 1B:
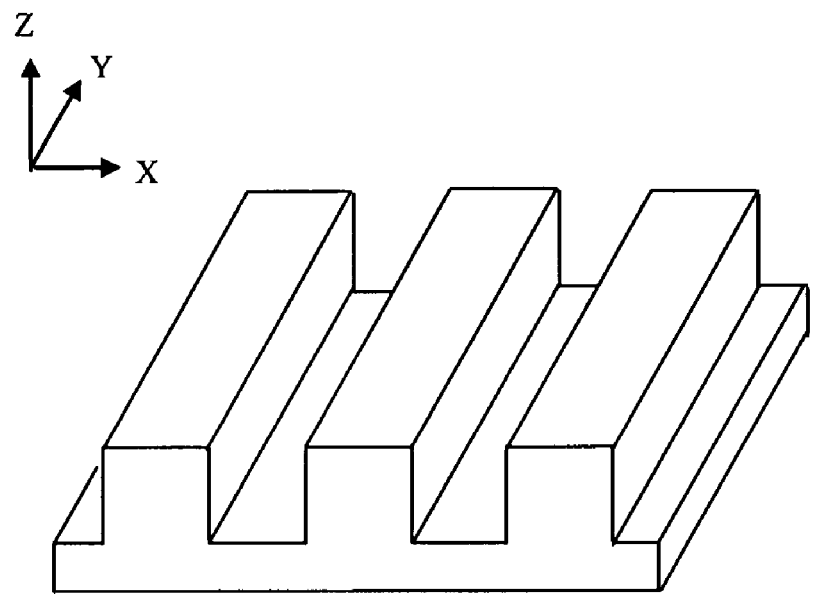
FIG. 1B depicts an exemplary one-dimension repeating structure.

The term "one-dimension structure" is used herein to refer to a structure having a profile that varies in one dimension. For example, FIG. 1B depicts a periodic grating having a profile that varies in one dimension (i.e., the x-direction). The profile of the periodic grating depicted in FIG. 1B varies in the z-direction as a function of the x-direction. However, the profile of the periodic grating depicted in FIG. 1B is assumed to be substantially uniform or continuous in-the y-direction.

Figure 1C:
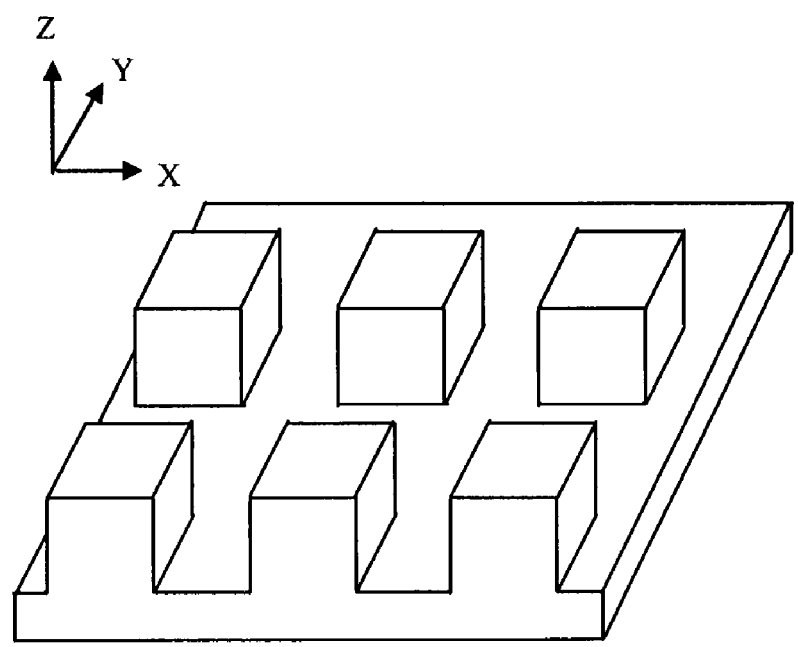
FIG. 1C depicts an exemplary two-dimension repeating structure

The term "two-dimension structure" is used herein to refer to a structure having a profile that varies in two-dimensions. For example, FIG. 1C depicts a periodic grating having a profile that varies in two dimensions (i.e., the x-direction and the y-direction). The profile of the periodic grating depicted in FIG. 1C varies in the z-direction.

Figure 2A:
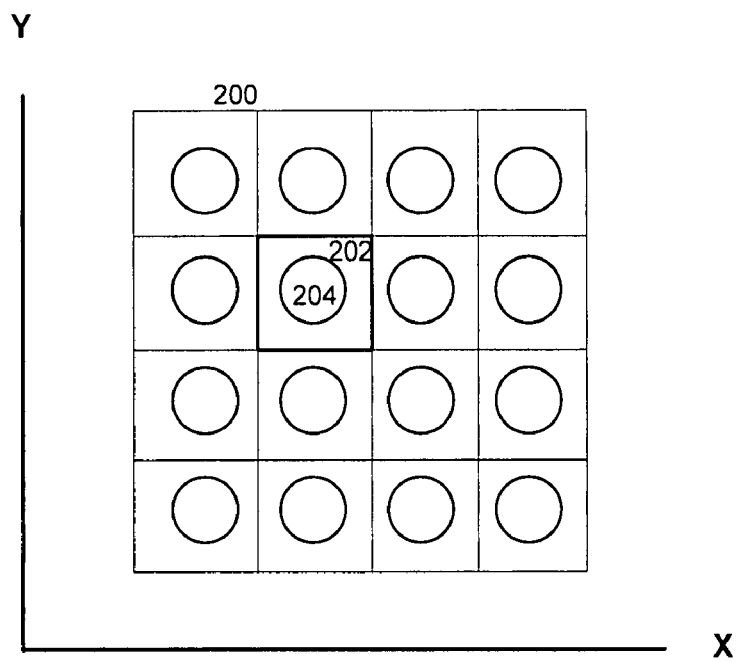
FIG. 2A depicts exemplary orthogonal grid of unit cells of a two-dimension repeating structure.

Discussion for FIGS. 2A, 2B, and 2C below describe the characterization of two-dimension repeating structures for optical metrology modeling. FIG. 2A depicts a top-view of exemplary orthogonal grid of unit cells of a two-dimension repeating structure. A hypothetical grid of lines is superimposed on the top-view of the repeating structure where the lines of the grid are drawn along the direction of periodicity. The hypothetical grid of lines forms areas referred to as unit cells. The unit cells may be arranged in an orthogonal or non-orthogonal configuration. Two-dimension repeating structures may comprise features such as repeating posts, contact holes, vias, islands, or combinations of two or more shapes within a unit cell. Furthermore, the features may have a variety of shapes and may be concave or convex features or a combination of concave and convex features. Referring to FIG. 2A, the repeating structure 200 comprises unit cells with holes arranged in an orthogonal manner. Unit cell 202 includes all the features and components inside the unit cell 202, primarily comprising a hole 204 substantially in the center of the unit cell 202.

Figure 2B:
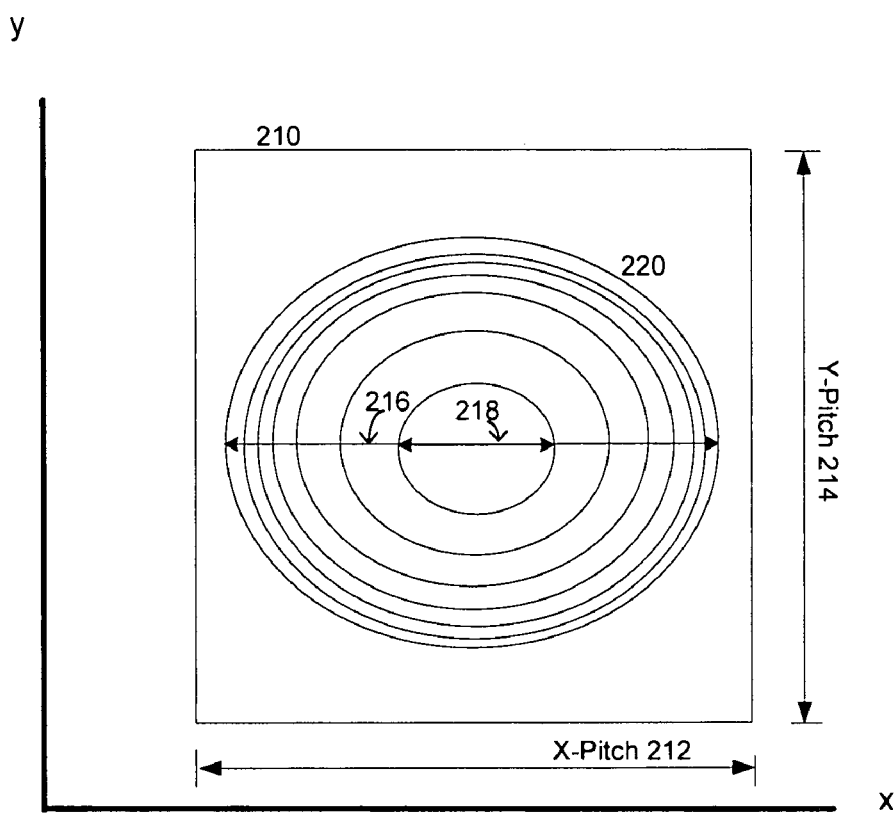
FIG. 2B depicts a top-view of a two-dimension repeating structure.

FIG. 2B depicts a top-view of a two-dimension repeating structure. Unit cell 210 includes a concave elliptical hole. FIG. 2B shows a unit cell 210 with a feature 220 that comprises an elliptical hole wherein the dimensions become progressively smaller until the bottom of the hole. Profile parameters used to characterize the structure includes the X-pitch 212 and the Y-pitch 214. In addition, the major axis of the ellipse 216 that represents the top of the feature 220 and the major axis of the ellipse 218 that represents the bottom of the feature 220 may be used to characterize the feature 220. Furthermore, any intermediate major axis between the top and bottom of the feature may also be used as well as any minor axis of the top, intermediate, or bottom ellipse, (not shown).

Figure 2C:
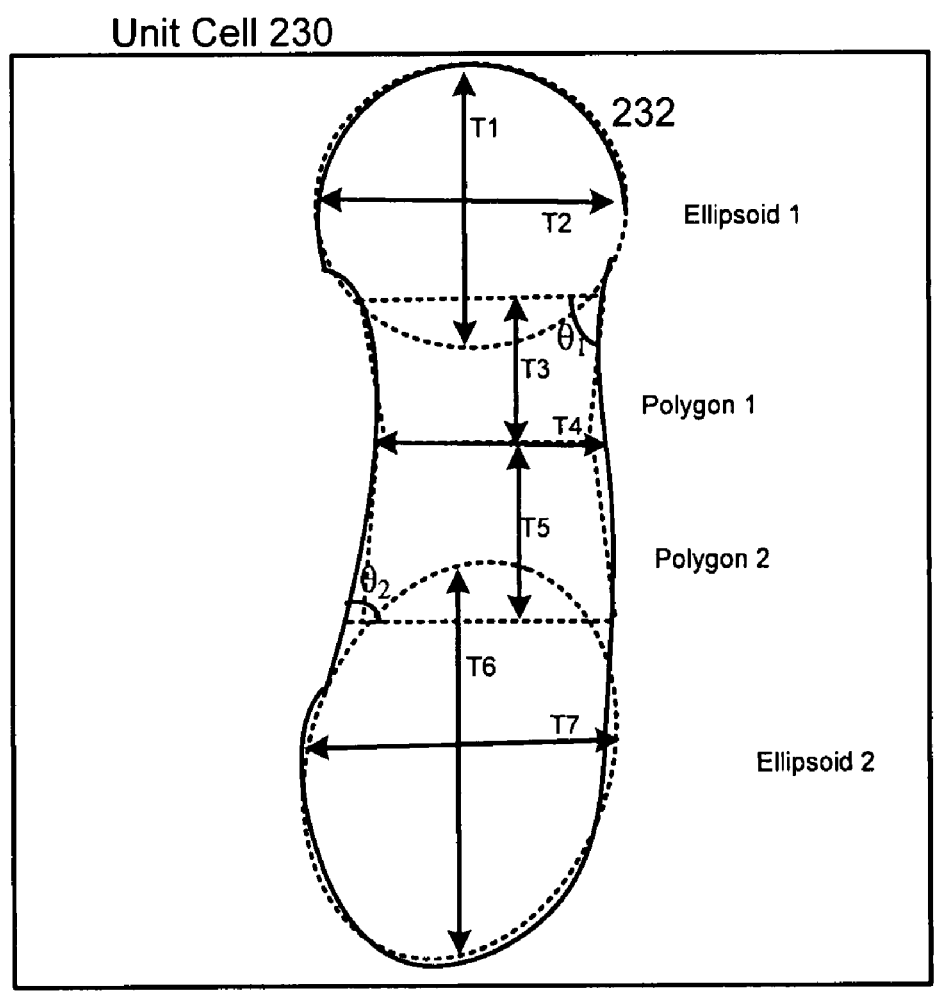
FIG. 2C is an exemplary technique for characterizing the top-view of a two-dimension repeating structure.

FIG. 2C is an exemplary technique for characterizing the top-view of a two-dimension repeating structure. A unit cell 230 of a repeating structure is a feature 232, an island with a peanut-shape viewed from the top. One modeling approach includes approximating the feature 232 with a variable number or combinations of ellipses and polygons. Assume further that after analyzing the variability of the top-view shape of the feature 232, it was determined that two ellipses, Ellipsoid 1 and Ellipsoid 2, and two polygons, Polygon 1 and Polygon 2 were found to fully characterize feature 232. In turn, parameters needed to characterize the two ellipses and two polygons comprise nine parameters as follows: T1 and T2 for Ellipsoid 1; T3, T4, and $\theta_1$ for Polygon 1; T4, T5, and $\theta_2$ for Polygon 2; and T6 and T7 for Ellipsoid 2. Many other combinations of shapes could be used to characterize the top-view of the feature 232 in unit cell 230. For a detailed description of modeling two-dimension repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference.

Figure 3:
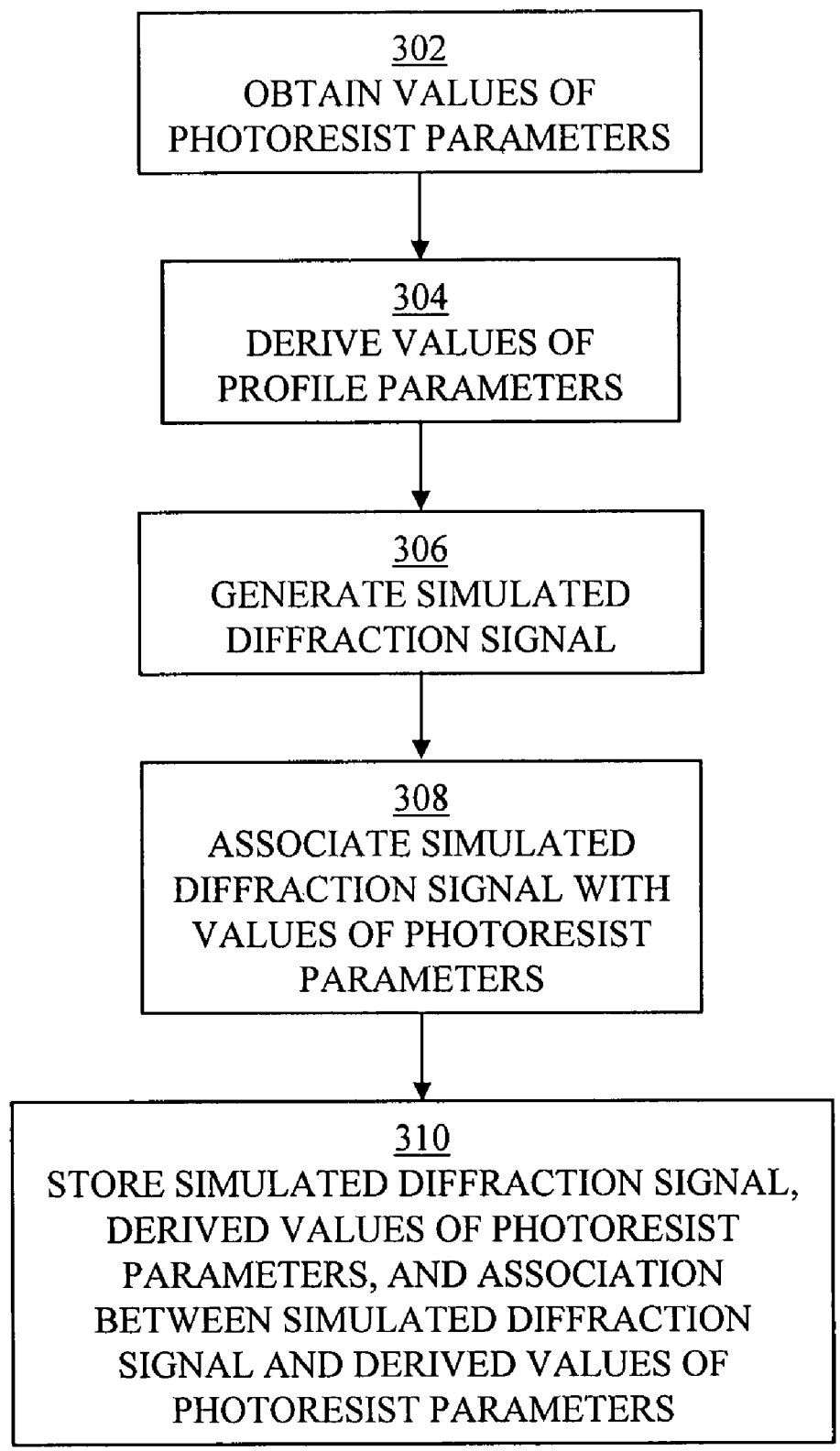
FIG. 3 is an exemplary process of generating a simulated diffraction signal.

FIG. 3 depicts an exemplary process for generating a simulated diffraction signal. As described below, the simulated diffraction signal is used to determine photoresist parameters of a wafer application to fabricate a structure on a wafer using optical metrology.

In step 302, one or more values of one or more photoresist parameters are obtained. For example, a user or operator can specify one or more values of one or more photoresist parameters of interest. Photoresist parameters characterize behavior of photoresist when the photoresist undergoes processing steps in the wafer application. As described in more detail below, exemplary photoresist parameters include change of inhibitor concentration, surface inhibition, diffusion during the photoresist baking process, labile absorptivity, non-labile absorptivity, intrinsic sensitivity of the photoresist (such as dose, focus, post-exposure bake (PEB), and post-apply bake (PAB) sensitivities), and the like.

In step 304, one or more values of one or more profile parameters are derived using the one or more values of the one or more photoresist parameters obtained in step 302. The one or more profile parameters characterize one or more geometric features of the structure, such as critical dimensions (top width, bottom width, etc.), height, top rounding, footing, and the like. Alternative processes for deriving the one or more values of the one or more profile parameters using the one or more values of the one or more photoresist parameters are described below.

In one exemplary embodiment, the one or more photoresist parameters of step 302 are selected prior to step 302. A user or operator can select the one or more photoresist parameters of interest for a particular wafer application and/or photolithography cluster. The one or more profile parameters of step 304 are also selected prior to step 304. The profile parameters selected are the profile parameters that have high correlation coefficients to the selected one or more photoresist parameters. In one embodiment, the correlation coefficients are 0.50 or higher.

In one embodiment, multivariate analysis can be used to determine the correlation coefficients of photoresist parameters to profile parameters. For example, the multivariate analysis can include a linear analysis or a nonlinear analysis. Additionally, for example, the multivariate analysis can include Principal Components Analysis (PCA), Independent Component Analysis, Cross Correlation Analysis, Linear Approximation Analysis, and the like. For a detailed description of a method of determining correlations of multiple process variables, refer to U.S. patent application Ser. No. 11/349,773, TRANSFORMING METROLOGY DATA FROM A SEMICONDUCTOR TREATMENT SYSTEM USING MULTIVARIATE ANALYSIS, by Vuong, et al., filed on May 8, 2006, and is incorporated in its entirety herein by reference.

In step 306, a simulated diffraction signal is generated using the one or more values of the one or more profile parameters derived in step 304. The simulated diffraction signal characterizes the behavior of light diffracted from the structure. In one exemplary embodiment, the simulated diffraction signal can be generated by calculating the simulated diffraction signal using a numerical analysis technique, such as rigorous coupled-wave analysis, with the one or more profile parameters as inputs. In another exemplary embodiment, the simulated diffraction signal can be generated using a machine learning algorithm, such as back-propagation, radial basis function, support vector, kernel regression, and the like. For more detail, see U.S. Pat. No. 6,913,900, entitled GENERATION OF A LIBRARY OF PERIODIC GRATING DIFFRACTION SIGNAL, by Niu, et al., issued on Sep. 13, 2005, and is incorporated in its entirety herein by reference.

In step 308, the simulated diffraction signal generated in step 306 is associated with the one or more values of the one or more photoresist parameters derived in step 302. Note, the simulated diffraction signal is generated using the one or more values of the one or more photoresist parameters rather than the one or more values of the one or more profile parameters.

In step 310, the generated simulated diffraction signal, the derived one or more values of the one or more photoresist parameters, and the association between the generated simulated diffraction signal and the derived one or more values of the one or more photoresist parameters are stored. The generated simulated diffraction signal, the derived one or more values of the one or more photoresist parameters, and the association between the generated simulated diffraction signal and the derived one or more values of the one or more photoresist parameters can be stored in a non-volatile storage medium, such as a compact disk (CD), digital video/versatile disk (DVD), flash drive, hard drive, and the like. The generated simulated diffraction signal, the derived one or more values of the one or more photoresist parameters, and the association between the generated simulated diffraction signal and the derived one or more values of the one or more photoresist parameters can also be stored in a volatile storage medium, such as in memory.

Figure 4:
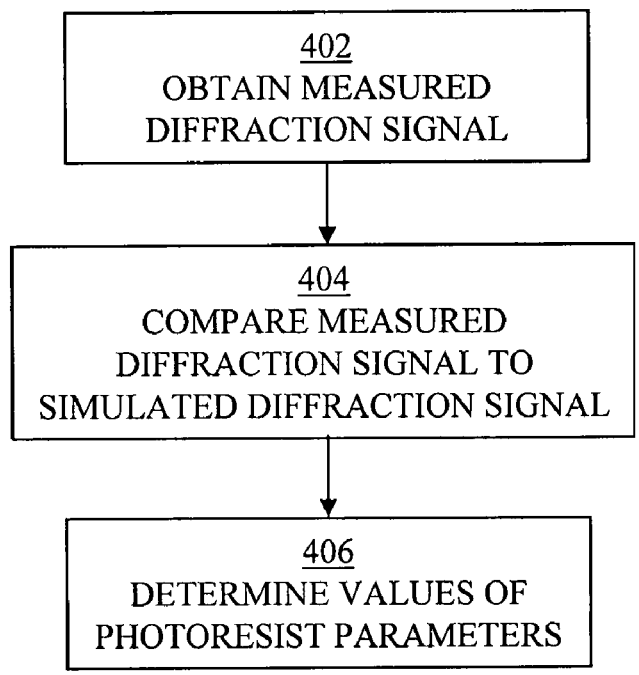
FIG. 4 is an exemplary process of determining one or more values of one or more photoresist parameters of a wafer application.

FIG. 4 depicts an exemplary process of determining one or more values of one or more photoresist parameters of a wafer application to fabricate a structure using the generated simulated diffraction signal. In step 402, after the structure has been fabricated using the wafer application, a measured diffraction signal is obtained off the structure. In step 404, the measured diffraction signal is compared with the stored simulated diffraction signal. In step 406, if the measured diffraction signal and the stored simulated diffraction signal match, such as within one or more matching criteria, then one or more values of one or more photoresist parameters of the wafer application are determined to be the one or more values of the one or more photoresist parameters associated with the matching simulated diffraction signal.

If the measured diffraction signal and the stored simulated diffraction signal do not match, then the measured diffraction signal is compared to another simulated diffraction signal associated with one or more values of one or more photoresist parameters that are different than those associated with the simulated diffraction signal that did not match the measured diffraction signal. With reference to FIG. 3, the another simulated diffraction signal can be generated by using different values for the one or more photoresist parameters in step 302 to derive different values for the one or more profile parameters in step 304, which are then used to generate the another simulated diffraction signal in step 306.

In one exemplary embodiment, the another simulated diffraction signal can be generated after determining that the measured diffraction signal does not match the stored simulated diffraction signal. In another exemplary embodiment, a plurality of simulated diffraction signals associated with different values of the one or more photoresist parameters can be generated in advance, then compared to the measured diffraction signal.

In particular, with reference again to FIG. 3, in step 302, a plurality of different values can be obtained for the one or more photoresist parameters. In step 304, a plurality of different values for the one or more profile parameters can be derived from the plurality of different values for the one or more photoresist parameters. In step 306, a plurality of different simulated diffraction signals can be generated using the plurality of different values for the one or more profile parameters. In step 308, the plurality of simulated diffraction signals are associated with the plurality of different values for the one or more photoresist parameters. In step 310, the plurality of simulated diffraction signals, the plurality of different values for the one or more photoresist parameters, and the association between the plurality of simulated diffraction signals and the plurality of different values for the one or more photoresist parameters are stored in a library.

Figure 5:
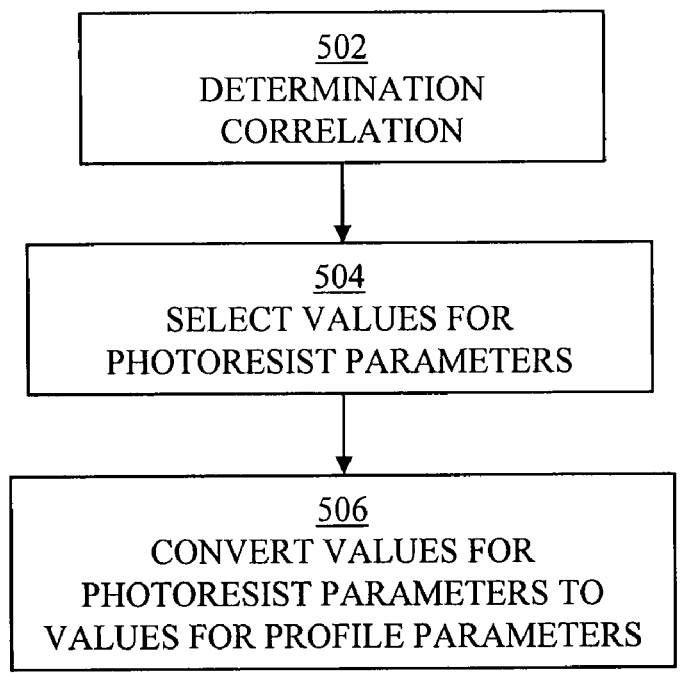
FIG. 5 is an exemplary process of deriving one or more profile parameters from one or more photoresist parameters.

FIG. 5 depicts an exemplary process of deriving one or more profile parameters from one or more photoresist parameters. In step 502, a correlation is determined between one or more photoresist parameters and the one or more profile parameters. In step 504, one or more values for the one or more photoresist parameters are selected. In step 506, the one or more values for the one or more photoresist parameters are converted to one or more values for the one or more profile parameters using the correlation determined in step 502. The simulated diffraction signal generated in step 306 (FIG. 3) is generated using the one or more values of the one or more profile parameters.

Figure 6:
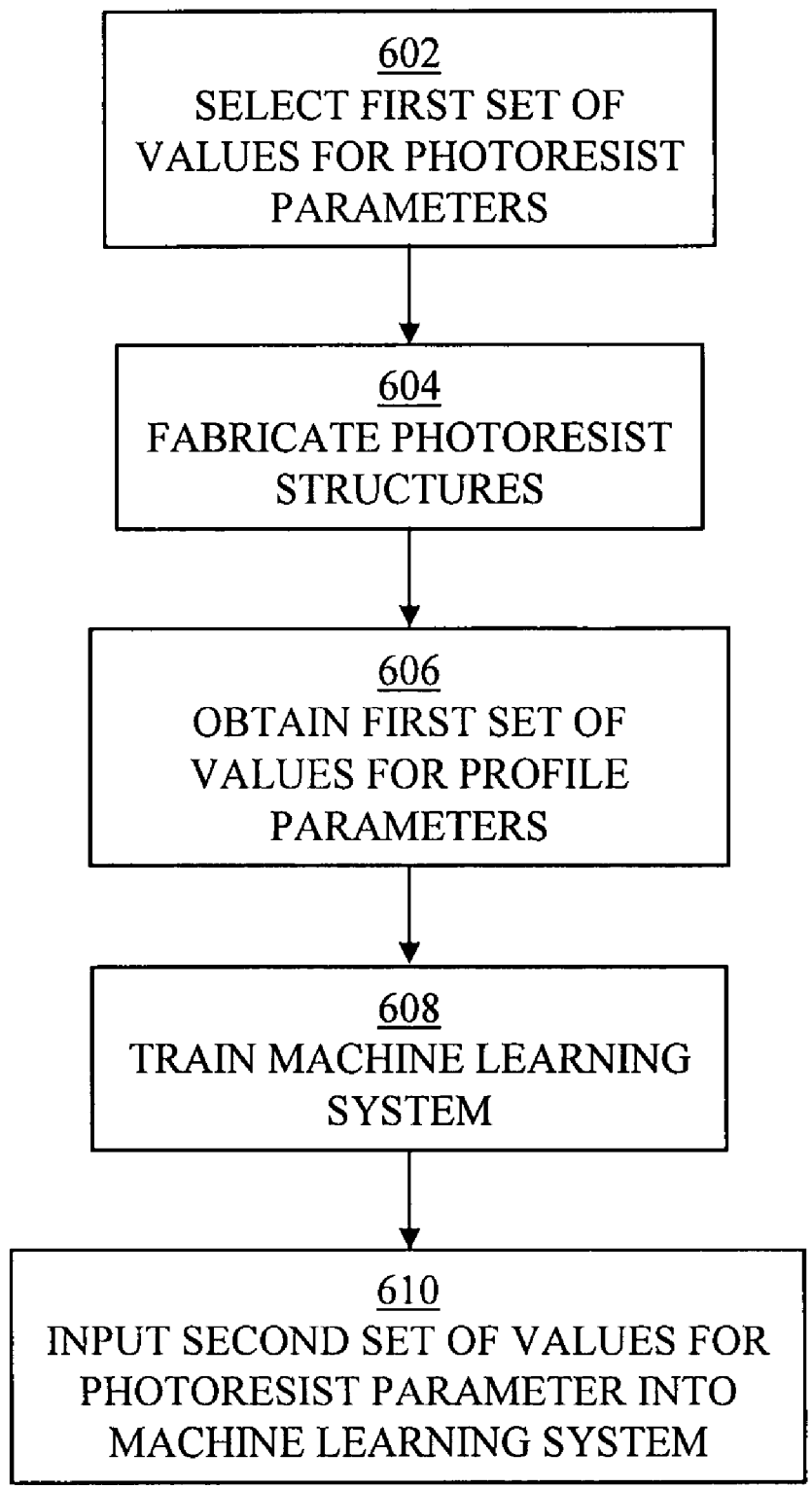
FIG. 6 is an exemplary process of determining a correlation between photoresist parameters and profile parameters.

FIG. 6 depicts an exemplary process of determining the correlation of step 502 (FIG. 5). In step 602, a first set of one or more values is selected for the one or more photoresist parameters. In step 604, one or more photoresist structures are fabricated utilizing the one or more values for the one or more photoresist parameters. In step 606, a first set of one or more values for the one or more profile parameters are obtained from the one or more photoresist structures. In step 608, a machine learning system is trained using the first set of one or more values for the one or more photoresist parameters as inputs to the machine learning system and the first set of one or more values for the one or more profile parameters as the expected outputs of the machine learning system. In step 610, after training the machine learning system, a second set of one or more values for the one or more photoresist parameter are inputted into the machine learning system to obtain a second set of one or more values for the one or more profile parameters as outputs of the machine learning system. The simulated diffraction signal generated in step 306 (FIG. 3) is generated using the second set of one or more values for the one or more profile parameters. The second set of one or more values for the one or more photoresist parameter is larger than the first set of one or more values for the one or more photoresist parameters. Similarly, the second set of one or more values for the one or more profile parameters is larger than the first set of one or more values for the one or more profile parameters.

In one exemplary embodiment, the first set of one or more values for the one or more profile parameters obtained in step 606 is obtained by measuring the one or more photoresist structures fabricated in step 602. The photoresist structures can be measured using a scanning electron microscope (SEM), which includes critical dimension SEM (CDSEM) and XSEM, and atomic force microscope (AFM).

In another exemplary embodiment, the first set of one or more values for the one or more profile parameters obtained in step 606 is obtained with a scatterometry device, such as a reflectometer, ellipsometer, and the like. In the case of a scatterometry device, a library, trained machine learning system, or a regression algorithm can be used to determine one or more values of the one or more profile parameters.

Figure 7:
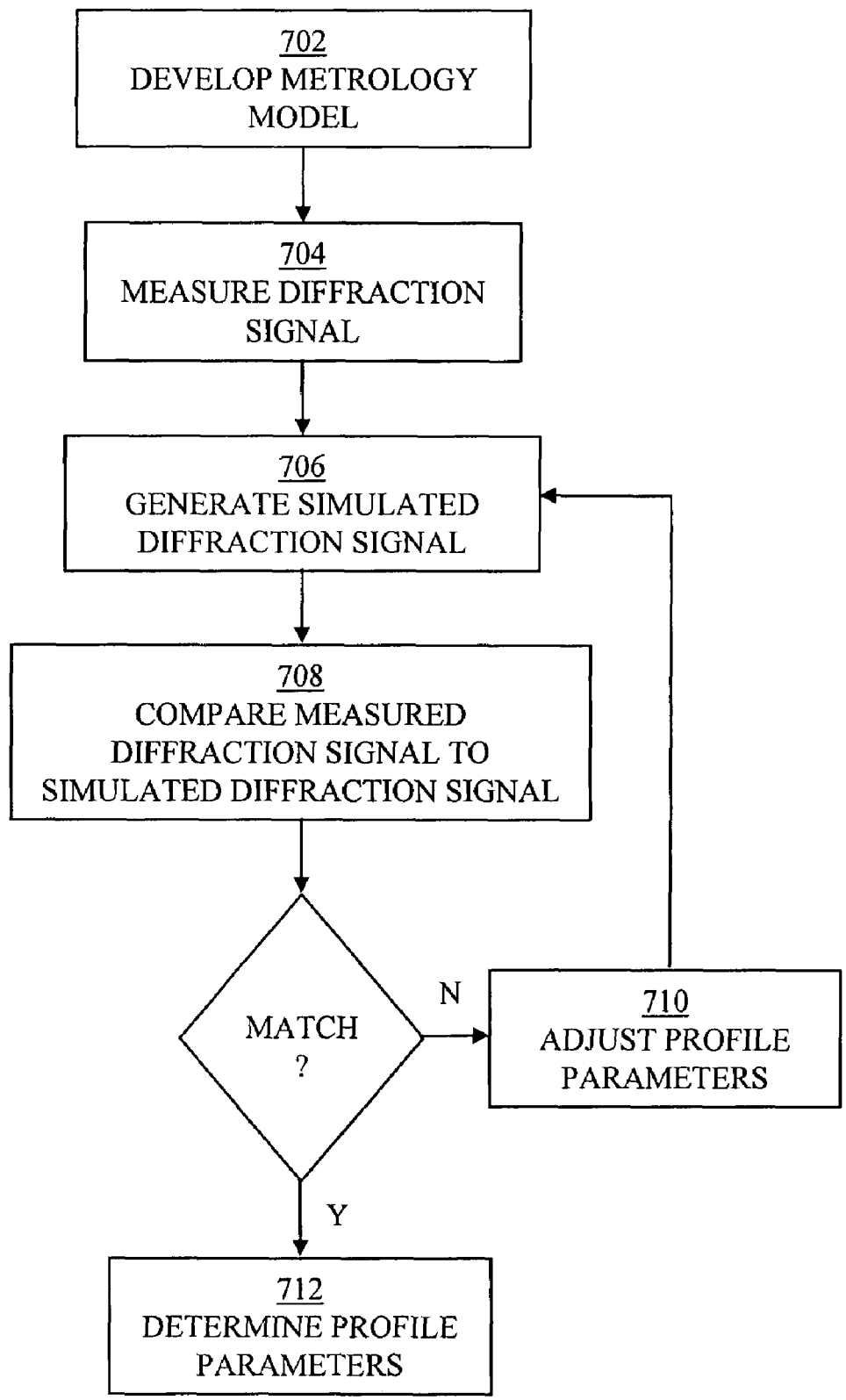
FIG. 7 is an exemplary process of determining profile parameters of photoresist parameters.

For example, with reference to FIG. 7, in step 702, a metrology model of the photoresist structure can be developed. The metrology model having a profile model, the profile model including the one or more profile parameters. In step 704, a diffraction signal is measured off the one or more photoresist structures using a scatterometry device. In step 706, a simulated diffraction signal is generated using an assumed set of profile parameters. In step 708, the measured diffraction signal is compared to the generated simulated diffraction signal to determine if one or more matching criteria are met. In step 710, if the one or more matching criteria are not met, the assumed set of profile parameters is adjusted and steps 706-710 are iterated. In step 712, if the one or more matching criteria are met, one or more profile parameters of the photoresist structure is assumed to be the assumed set of profile parameters used in generating the matching simulated diffraction signal.

With reference again to FIG. 6, in one exemplary embodiment, the first set of one or more values for the one or more profile parameters obtained in step 606 is obtained by selecting one or more values for the one or more photoresist parameters. A photoresist fabrication process is simulated using the selected one or more values for the one or more photoresist parameters to generate one or more values for the one or more profile parameters. The photoresist fabrication process can be simulated using process simulators such as Athena™ from Silvaco International, Prolith™ from KLA-Tencor, Solid-C from Sigma-C Gmbh, TCAD™ from Synopsis, and the like.

In performing the simulation, in one exemplary embodiment, a first subset of one or more photoresist parameters and one or more fabrication parameters is set to constants. One or more ranges of values for a second subset of one or more photoresist are set. The simulation of the photoresist fabrication process is then performed with the first subset set to the constants and the second subset set to float over the set ranges of values.

Figure 8:
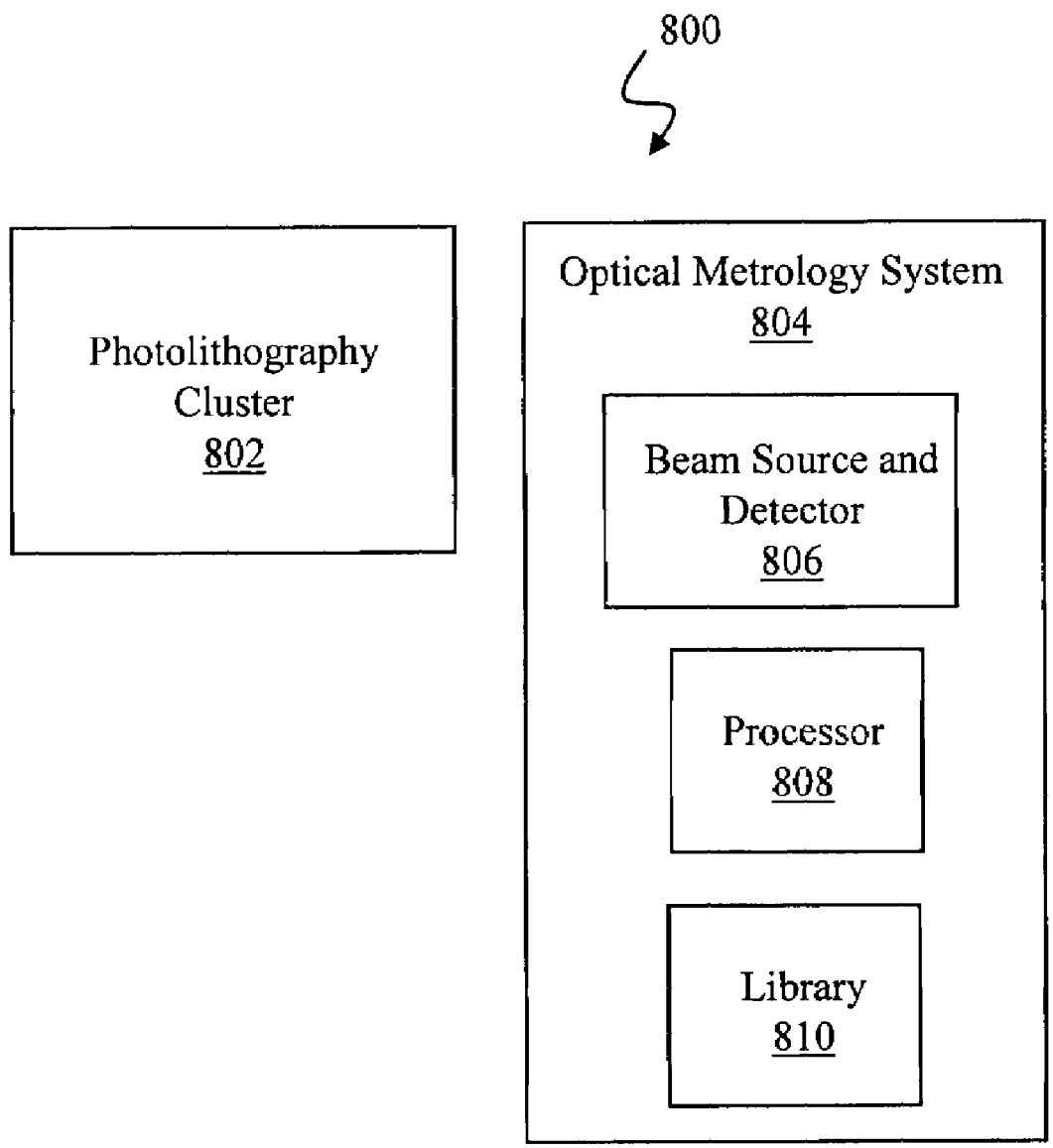
FIG. 8 is a block diagram of an exemplary system to generate a simulated diffraction signal.

FIG. 8 depicts an exemplary system 800 to generate a simulated diffraction signal to determine photoresist parameters of a wafer application to fabricate a structure on a wafer using optical metrology. System 800 includes a photolithography cluster 802 and an optical metrology system 804.

Photolithography cluster 802 is configured to perform a wafer application to fabricate a structure on a wafer. As described above, one or more photoresist parameters characterize the behavior of photoresist when the photoresist undergoes processing steps in the wafer application performed using photolithography cluster 802.

Optical metrology system 804 is similar to optical metrology system 40 (FIG. 1A). In one exemplary embodiment, optical metrology system 804 includes a beam source and detector 806 and metrology processor 808. Beam source and detector 806 are configured to measure a diffraction signal off the structure. Processor 808 is configured to compare the measured diffraction signal to a simulated diffraction signal.

As described above, the simulated diffraction signal is associated with one or more values of one or more photoresist parameters. The simulated diffraction signal was generated using one or more values of one or more profile parameters. The one or more values of the one or more profile parameters used to generate the simulated diffraction signal were obtained from the one or more values of the one or more photoresist parameters associated with the simulated diffraction signal. If the measured diffraction signal and the stored simulated diffraction signal match, one or more values of one or more photoresist parameters in the fabrication application are determined to be the one or more values of the one or more photoresist parameters associated with the stored simulated diffraction signal.

In one exemplary embodiment, optical metrology system 804 can also include a library 810 with a plurality of simulated diffraction signals and a plurality of values of one or more photoresist parameters associated with the plurality of simulated diffraction signals. As described above, the library can be generated in advance, metrology processor 808 can compare a measured diffraction signal off a structure to the plurality of simulated diffraction signals in the library When a matching simulated diffraction signal is found, the one or more values of the one or more photoresist parameters associated with the matching simulated diffraction signal in the library is assumed to be the one or more values of the one or more photoresist parameters used in the wafer application to fabricate the structure.

Figure 9:
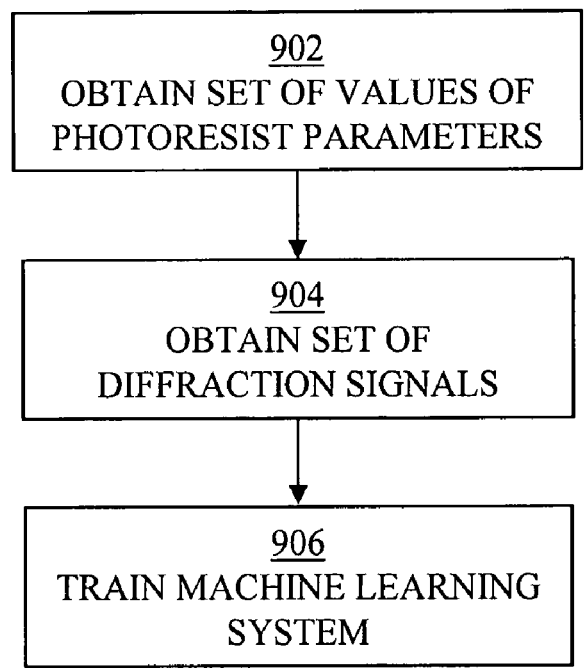
FIG. 9 is an exemplary for training a machine learning system.

FIG. 9 depicts an exemplary process for training a machine learning system. As described below, the trained machine learning system is used to determine photoresist parameters of a wafer application to fabricate a structure on a wafer using optical metrology.

In step 902, a set of different values of one or more photoresist parameters are obtained. For example, a user or operator can specify different values of one or more photoresist parameters of interest. As described above, photoresist parameters characterize behavior of photoresist when the photoresist undergoes processing steps in the wafer application. For example, exemplary photoresist parameters include change of inhibitor concentration, surface inhibition, diffusion during the photoresist baking process, labile absorptivity, non-labile absorptivity, intrinsic sensitivity of the photoresist (such as dose, focus, post-exposure bake (PEB), and post-apply bake (PAB) sensitivities), and the like.

In step 904, a set of diffraction signals is obtained using the set of different values of the one or more photoresist parameters. In step 906, a machine learning system is trained using the set of diffraction signals as inputs to the machine learning system and the set of different values for the one or more photoresist parameters as the expected outputs of the machine learning system.

In one exemplary embodiment, the set of diffraction signals obtained in step 904 is obtained by fabricating a set of photoresist structures utilizing the set of different values of the one or more photoresist parameters obtained in step 902. The set of diffraction signals is measured off the set of photoresist structures using a reflectometer or ellipsometer.

In another exemplary embodiment, the set of diffraction signals obtained in step 904 is obtained by simulating a fabrication process utilizing the set of different values of the one or more photoresist parameters to generate a set of different values for one or more profile parameters of photoresist structures. The set of diffraction signals is then generated utilizing the set of different values for the one or more profile parameters. The fabrication process can be simulated utilizing a photolithography simulator. As described above, the set of diffraction signals can be generated utilizing a numerical analysis technique, including rigorous coupled-wave analysis. Alternatively, the set of diffraction signals can be generated utilizing another machine learning system.

Figure 10:
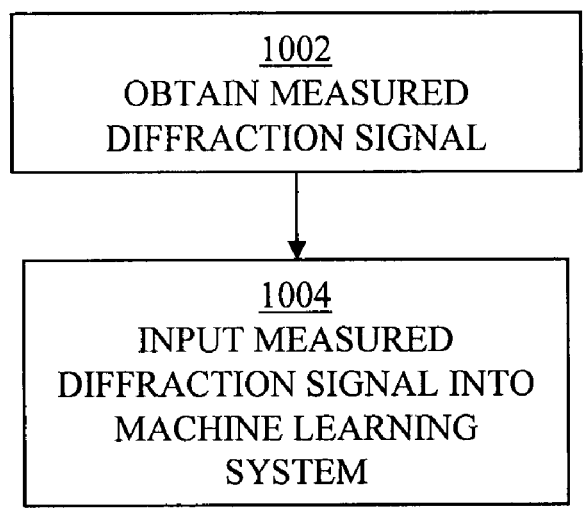
FIG. 10 is an exemplary process of determining one or more values of one or more photoresist parameters.

FIG. 10 depicts an exemplary process of determining one or more values of one or more photoresist parameters of a wafer application to fabricate a structure using the generated simulated diffraction signal. In step 1002, after the structure has been fabricated using the wafer application, a measured diffraction signal is obtained off the structure. The set of diffraction signals can be measured using a scatterometry device, such as a reflectometer, ellipsometer, and the like. In step 1004, after training the machine learning system, the measured diffraction signal is inputted into the trained machine learning system to obtain one or more values of one or more photoresist parameters as an output of the trained machine learning system.

Figure 11:
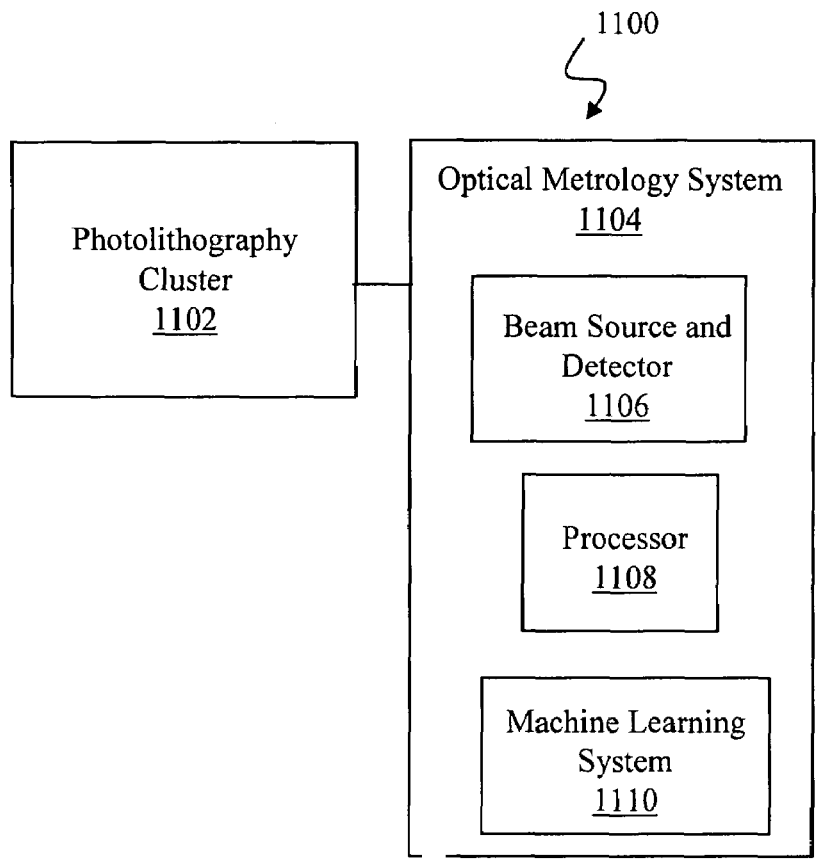
FIG. 11 is a block diagram of an exemplary system to train and use a machine learning system.

FIG. 11 depicts an exemplary system 1100 to train and use a machine learning system to determine photoresist parameters of a wafer application to fabricate a structure on a wafer using optical metrology. System 1100 includes a photolithography cluster 1102 and an optical metrology system 1104.

Photolithography cluster 1102 is configured to perform a wafer application to fabricate a structure on a wafer. As described above, one or more photoresist parameters characterize the behavior of photoresist when the photoresist undergoes processing steps in the wafer application performed using photolithography cluster 1102.

Optical metrology system 1104 includes a beam source and detector 1106, processor 1108, and machine learning system 1110. Beam source and detector 1106 can be components of a scatterometry device, such as a reflectometer, ellipsometer, and the like.

As described above, in one exemplary embodiment, a set of photoresist structures is fabricated utilizing a set of different values for one or more photoresist parameters and photolithography cluster 1102. Beam source and detector 1106 are configured to measure a set of diffraction signals off the set of photoresist structures. Processor 1108 is configured to train machine learning system 1110 using the set of measured diffraction signals as inputs to machine learning system 1110 and the set of different values for the one or more photoresist parameters as the expected outputs of machine learning system 1110.

After machine learning system 1110 has been trained, optical metrology system 1100 can be used to determine one or more values of one or more photoresist parameters of a wafer application to fabricate a structure. In particular, a structure is fabricated using photolithography cluster 1102 or another photolithography cluster. A diffraction signal is measured off the structure using beam source and detector 1106. The measured diffraction signal is inputted into the trained machine learning system 1110 to obtain one or more values of one or more photoresist parameters as an output of the trained machine learning system 1110.

Figure 12:
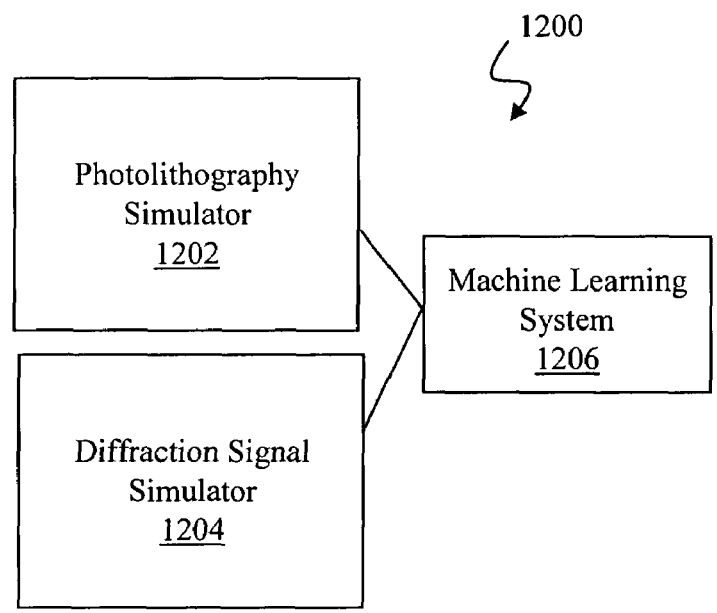
FIG. 12 is a block diagram of another exemplary system to train and use a machine learning system.

FIG. 12 depicts an exemplary system 1200 to train and use a machine learning system to determine photoresist parameters of a wafer application to fabricate a structure on a wafer using optical metrology. System 1200 includes a photolithography simulator 1202, a diffraction signal simulator 1204, and a machine learning system 1206.

Photolithography simulator 1202 is configured to simulate fabrication of a set of photoresist structures using a set of different values of one or more photoresist parameters. As described above, one or more photoresist parameters characterize the behavior of photoresist when the photoresist undergoes processing steps in the wafer application, such as a photolithography process using a photolithography cluster.

Diffraction signal simulator 1204 is configured to simulate a set of diffraction signals off the set of photoresist structures generated by photolithography simulator 1202. In particular, a set of different values for one or more profile parameters of photoresist structures can be generated using photolithography simulator 1202. Diffraction signal simulator 1204 can then generate the set of diffraction signals using the set of different values for the one or more profile parameters of the photoresist structures. Diffraction signal simulator 1204 can generate the set of diffraction signals using a numerical analysis technique, including rigorous coupled-wave analysis, or another machine learning system.

Machine learning system 1206 can be trained by utilizing the set of diffraction signals as inputs to machine learning system 1206 and the set of different values of the one or more photoresist parameters as expected outputs of machine learning system 1206. After machine learning system 1206 has been trained, a measured diffraction signal off a structure to be examined can be inputted into machine learning system 1206 to obtain one or more values of one or more photoresist parameters as an output of machine learning system 1206.

Figure 13:
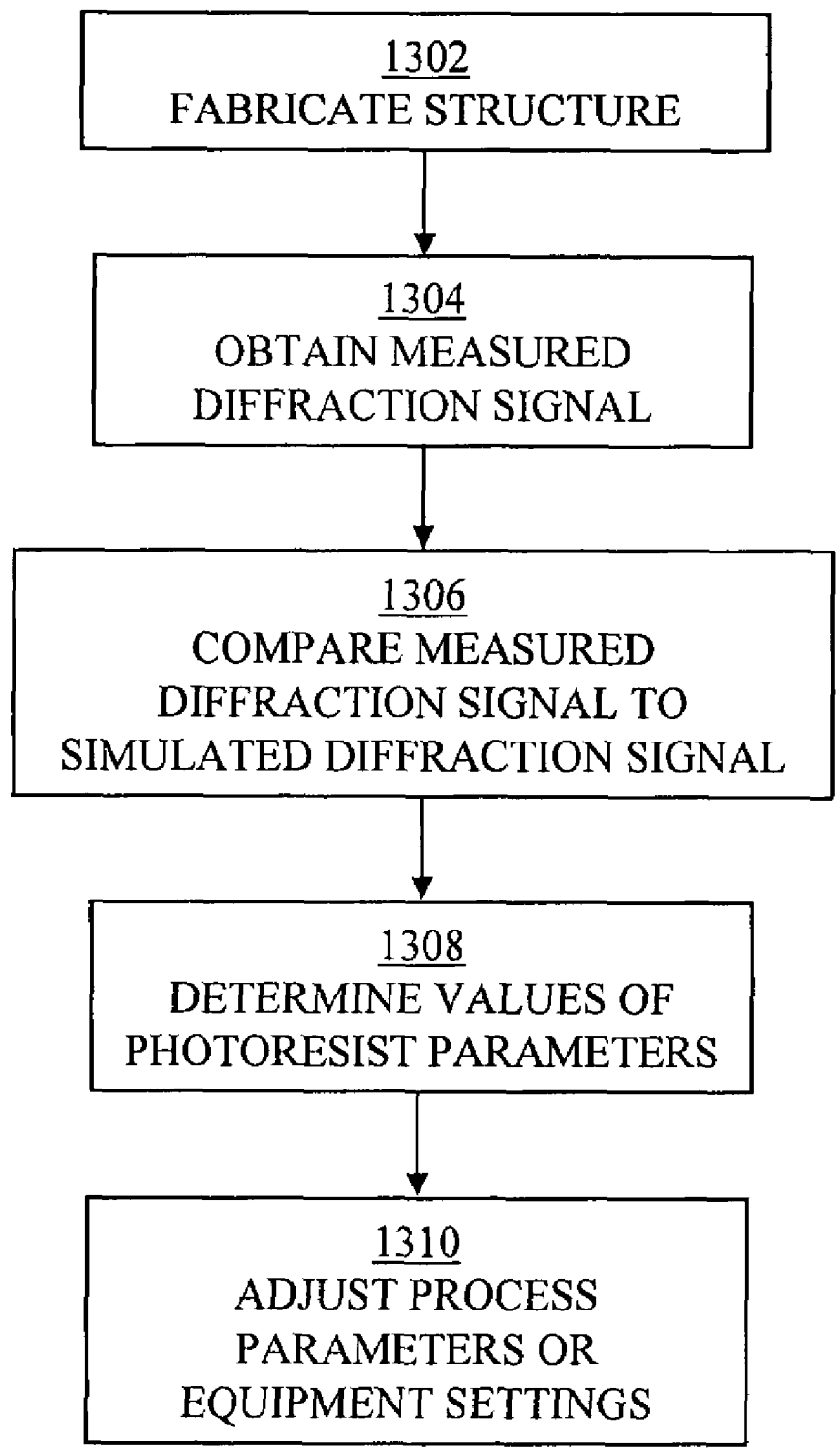
FIG. 13 is an exemplary process of controlling a photolithography cluster.

FIG. 13 depicts an exemplary process of controlling a photolithography cluster. In step 1302, a wafer application is performed using a photolithography cluster to fabricate a structure on a wafer. In step 1304, after the structure has been fabricated using the photolithography cluster, a measured diffraction signal is obtained off the structure.

In step 1306, the measured diffraction signal is compared with a simulated diffraction signal. As described above, the simulated diffraction signal is associated with one or more photoresist parameters. The simulated diffraction signal was generated using one or more profile parameters. The one or more profile parameters used to generate the simulated diffraction signal were obtained from the one or more photoresist parameters associated with the simulated diffraction signal.

In step 1308, if the measured diffraction signal and the simulated diffraction signal match, such as within one or more matching criteria, then one or more values of one or more photoresist parameters of the wafer application are determined to be the one or more values of the one or more photoresist parameters associated with the matching simulated diffraction signal. In step 1310, one or more process parameters or equipment settings of the photolithography cluster are adjusted based on the one or more values of the one or more photoresist parameters.

In one exemplary embodiment, one or more process parameters or equipment settings of another fabrication cluster are adjusted based on the one or more values of the one or more photoresist parameters. The fabrication cluster can process a wafer before or after the wafer is processed in the photolithography cluster. For example, the photolithography cluster can perform a post exposure bake process. The fabrication cluster can perform an exposure process prior to the post exposure bake process performed in the photolithography cluster. Alternatively, the fabrication cluster can perform an etch process subsequent to the post exposure bake process performed in the photolithography cluster. The fabrication cluster can also perform an etch, chemical vapor deposition, physical vapor deposition, chemical-mechanical planarization, and/or thermal process after the photolithographic process performed in the photolithography cluster.

Figure 14:
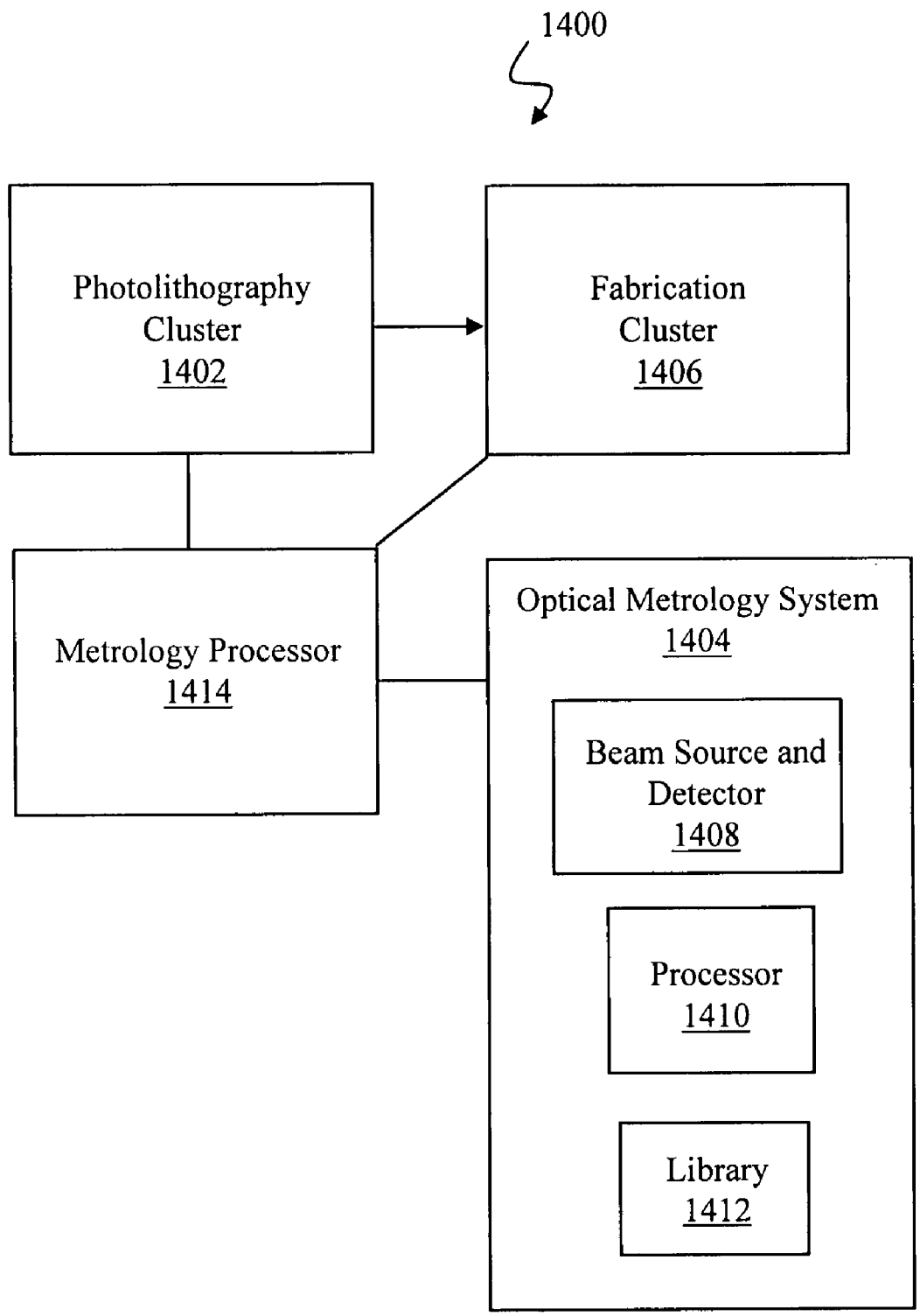
FIG. 14 is a block diagram of an exemplary system to control a photolithography cluster.

FIG. 14 depicts an exemplary system 1400 to control a photolithography cluster. System 1400 includes a photolithography cluster 1402 and optical metrology system 1404. System 1400 also includes a fabrication cluster 1406. Although fabrication cluster 1406 is depicted in FIG. 14 as being subsequent to photolithography cluster 1402, it should be recognized that fabrication cluster 1406 can be located prior to photolithography cluster 1402 in system 1400.

A photolithographic process, such as exposing and/or developing a photoresist layer applied to a wafer, can be performed using photolithography cluster 1402. As described above, one or more photoresist parameters characterize the behavior of photoresist when the photoresist undergoes processing steps in the wafer application performed using photolithography cluster 1402.

Optical metrology system 1404 is similar to optical metrology system 40 (FIG. 1A). In one exemplary embodiment, optical metrology system 1404 includes a beam source and detector 1408 and processor 1410. Beam source and detector 1408 are configured to measure a diffraction signal off the structure. Processor 1410 is configured to compare the measured diffraction signal to a simulated diffraction signal.

As described above, the simulated diffraction signal is associated with one or more values of one or more photoresist parameters. The simulated diffraction signal was generated using one or more values of one or more profile parameters. The one or more values of the one or more profile parameters used to generate the simulated diffraction signal were obtained from the one or more values of the one or more photoresist parameters associated with the simulated diffraction signal. If the measured diffraction signal and the stored simulated diffraction signal match, one or more values of one or more photoresist parameters in the fabrication application are determined to be the one or more values of the one or more photoresist parameters associated with the stored simulated diffraction signal.

In one exemplary embodiment, optical metrology system 1404 can also include a library 1412 with a plurality of simulated diffraction signals and a plurality of values of one or more photoresist parameters associated with the plurality of simulated diffraction signals. As described above, the library can be generated in advance, metrology processor 1410 can compare a measured diffraction signal off a structure to the plurality of simulated diffraction signals in the library When a matching simulated diffraction signal is found, the one or more values of the one or more photoresist parameters associated with the matching simulated diffraction signal in the library is assumed to be the one or more values of the one or more photoresist parameters used in the wafer application to fabricate the structure.

System 1400 also includes a metrology processor 1414. In one exemplary embodiment, processor 1410 can transmit the one or more values of the one or more photoresist parameters to metrology processor 1414. Metrology processor 1414 can then adjust one or more process parameters or equipment settings of photolithography cluster 1402 based on the one or more values of the one or more photoresist parameters determined using optical metrology system 1404. Metrology processor 1414 can also adjust one or more process parameters or equipment settings of fabrication cluster 1406 based on the one or more values of the one or more photoresist parameters determined using optical metrology system 1404. As noted above, fabrication cluster 1406 can process the wafer before or after photolithography cluster 1402.

As described above, change of inhibitor concentration is an exemplary photoresist parameter. Change of inhibitor concentration is typically expressed by Dill's ABC parameters and equations. The change of the inhibitor concentration, i.e., the change of chemical compounds that inhibit development of the photoresist, M, is the ratio of the photo-active compound (PAC) c at a certain time related to the PAC $c_0$ when the exposure begins:

$$M = \frac{c}{c_0} \quad (1.10)$$

The A and the B along with the M define the absorption of the photoresist via:

$$\alpha = A \cdot M + B \quad (1.20)$$

The absorption $\alpha$ defines the attenuation of the intensity with the depth z. $I_0$ is the intensity at the surface of the photoresist.

$$I(z) = I_0 \cdot e^{-\alpha z} I(z) = I_0 \cdot e^{-\alpha z} \quad (1.30)$$

The change of M with the time is expressed by the differential equation:

$$\frac{dM}{dt} = -C \cdot I \cdot M \quad (1.40)$$

The Dill's ABC parameters are further described as follows. A is the absorption change or exposure dependent absorption. At the beginning of photoresist development, t=0, M=1 by definition. Later, M is decreasing and sometimes even goes down to 0. Thus, the A·M term is reduced while the exposed photoresist is bleaching. B is the constant base absorption since B does not change the $\alpha$ with changing M. Bigger values of B (dyeing of the photoresist) cause shallow side wall angle, but on the other hand suppress unwanted back reflections from the underlying substrate. C is the quantum efficiency of the photo-chemical reaction.

Surface inhibition is another exemplary photoresist parameter. For chemically amplified photoresist (CAR), surface inhibition is characterized by a diffusion coefficient and an absorption constant through the boundary. CAR can also be described by means of the Dill ABC parameters with M being replaced by PAG (photo acid generator). The PAG decays to generate acid, so after exposure the normalized acid concentration is $a = 1 - PAG \cdot t_{exp}$.

An effective acid concentration is obtained from a by diffusion in vertical direction with appropriate boundary conditions:

$$\frac{\partial a_{\mathit{eff}}}{\partial t} = D \frac{\partial^2 a_{\mathit{eff}}}{\partial z^2} \text{ and } D \frac{\partial a_{\mathit{eff}}}{\partial z}\bigg|_{boundary} = h \cdot a_{\mathit{eff}}|\text{boundary}.$$

With D being the diffusion coefficient and h the absorption constant. An analytical solution (see, e.g., SOLID-C manual chapter 8 "Delay effects for chemically amplified resists") of this differential equation can be found by assuming that $a_{\mathit{eff}}(x,y,z,t) = c_{\mathit{fak}}(z,t) * a(x,y,z)$ and infinite photoresist thickness. $c_{\mathit{fak}}$ obeys the diffusion equation.

Diffusion is another exemplary photoresist parameter. During the post exposure bake, diffusion of the photoactive compound takes place. An important parameter of the diffusion is the diffusion length. The diffusion length should exceed $\lambda/4n$ since the most important function of diffusion is to flatten out the standing wave pattern in the photoresist imposed by the exposure. On the other hand, diffusion must not be too great in order not to degrade the aerial image.

In general, diffusion is described by a differential equation+boundary conditions such as:

$$\frac{\partial M}{\partial t} = D \cdot \Delta M \text{ with the } \Delta \text{ operator}$$

$$\Delta = \frac{\partial^2}{\partial x^2} + \frac{\partial^2}{\partial y^2} + \frac{\partial^2}{\partial z^2}.$$

M is the PAC (photo active compound) concentration and t is the PEB time. Choosing either the linear or the exponential model, D can be given as Linear: $D(a)=D1+(D2-D1)*a$ Exponential: $D(a)=D1*\exp(c0*a)$, where a is the normalized acid concentration for CAR. The diffusion length $\sigma$ is related to the bake time t and the diffusion coefficient D by:

$$2tD = \sigma^2.$$

Development rate is another exemplary photoresist parameter. There are several development models with a specific set of development parameters and equations. Basically, the development models relate the development rate to the inhibitor concentration M after exposure. Below are two examples:
(1) Dill's model:

$$R = \exp(R_1 + R_2 \cdot M + R_3 \cdot M^2). \quad (1.50)$$

(2) Chris Mack's model:

$$R = R_{max} \frac{(a+1) \cdot (1-M)^n}{a + (1-M)^n} + R_{min}. \quad (1.60)$$

It is apparent that the $R_1$ in the Dill model and the $R_{min}$ in the Mack model are development rates for the unexposed photoresist. Alternatively, the one or more photoresist parameters may include exposure parameters such as labile absorptivity, non-labile absorptivity, and/or intrinsic sensitivity of the photoresist (such as dose, focus, post-exposure bake (PEB), and post-apply bake (PAB) sensitivities). For a detailed description of photoresist parameters that may be selected for correlation to the diffraction signal, refer to Arthur, Graham G., et al., "Enhancing the Development-rate Model for Optimum Simulation Capability in the Subhalfmicron Regime," Proc. SPIE Vol. 3049, p. 189-200, Advances in Resist Technology and Processing XIV, Regine G. Tarascon-Auriol; Ed., July 1997; and SOLID-C manual, chapter 10 Resist Image Formation.

Although exemplary embodiments have been described, various modifications can be made without departing from the spirit and/or scope of the present invention. Therefore, the present invention should not be construed as being limited to the specific forms shown in the drawings and described above.

We claim:

1. A method of controlling a photolithography cluster using optical metrology, the method comprising:
a) fabricating a structure on a wafer using a photolithography cluster;
b) obtaining a measured diffraction signal off the structure;
c) comparing the measured diffraction signal to a simulated diffraction signal, wherein the simulated diffraction signal is associated with one or more values of one or more photoresist parameters, wherein the one or more photoresist parameters characterize behavior of photoresist when the photoresist undergoes processing steps in the photolithography cluster, wherein the simulated diffraction signal was generated using one or more values of one or more profile parameters, and wherein the one or more values of the one or more profile parameters used to generate the simulated diffraction signal were derived from the one or more values of the one or more photoresist parameters associated with the simulated diffraction signal;
d) if the measured diffraction signal and the simulated diffraction signal match, then determining one or more values of one or more photoresist parameters used in the photolithography cluster to be the one or more values of the one or more photoresist parameters associated with the matching simulated diffraction signal; and
e) adjusting one or more process parameters or equipment settings of the photolithography cluster based on the one or more values of the one or more photoresist parameters determined in d).

2. The method of claim 1, further comprising:
if the measured diffraction signal and the simulated diffraction signal compared in c) do not match, comparing the measured diffraction signal to another simulated diffraction signal associated with one or more values of one or more photoresist parameters that are different than the one or more values of the one or more photoresist parameters of the simulated diffraction signal that did not match the measured diffraction signal.

3. The method of claim 2, wherein the simulated diffraction signal and the another simulated diffraction signal are stored in a library having a plurality of simulated diffraction signals and a plurality of values of one or more photoresist parameters associated with the plurality of simulated diffraction signals.

4. The method of claim 2, wherein the another simulated diffraction signal was generated after the measured diffraction signal and the simulated diffraction signal compared in c) are determined not to match.

5. The method of claim 1, wherein the one or more photoresist parameters comprise change of inhibitor concentration, surface inhibition, diffusion during the photoresist baking process, development rate parameters, labile absorptivity, non-labile absorptivity, and/or intrinsic sensitivity of photoresist.

6. The method of claim 1, further comprises:
prior to c)-e), determining a correlation between the one or more photoresist parameters and the one or more profile parameters;
prior to c)-e), obtaining one or more values for the one or more photoresist parameters; and
prior to c)-e), converting the one or more values for the one or more photoresist parameters to one or more values for the one or more profile parameters using the determined correlation, wherein the simulated diffraction signal is generated using the one or more values for the one or more profile parameters.

7. The method of claim 1, further comprises:
- prior to c)-e), selecting a first set of one or more values for the one or more photoresist parameters;
- prior to c)-e), fabricating one or more photoresist structures utilizing the one or more values for the one or more photoresist parameters;
- prior to c)-e), obtaining a first set of one or more values for the one or more profile parameters from the one or more photoresist structures;
- prior to c)-e), training a machine learning system using the first set of one or more values for the one or more photoresist parameters as inputs to the machine learning system and the first set of one or more values for the one or more profile parameters as the expected outputs of the machine learning system; and
- prior to c)-e), after training the machine learning system, inputting a second set of one or more values for the one or more photoresist parameters into the machine learning system to obtain a second set of one or more values for the one or more profile parameters as outputs of the machine learning system, wherein the simulated diffraction signal is generated using the second set of one or more values for the one or more profile parameters.

8. The method of claim 1, further comprising:
- adjusting one or more process parameters or equipment settings of a fabrication cluster based on the one or more values of the one or more photoresist parameters determined in d).

9. The method of claim 8, wherein the fabrication cluster processes wafers prior to the photolithography cluster.

10. The method of claim 8, wherein the fabrication cluster processes wafers subsequent to the photolithography cluster.

11. A computer-readable storage medium containing computer-executable instructions to control a photolithography cluster using optical metrology, comprising instructions for:
- a) obtaining a measured diffraction signal off a structure fabricated on a wafer using a photolithography cluster;
- b) comparing the measured diffraction signal to a simulated diffraction signal, wherein the simulated diffraction signal is associated with one or more values of one or more photoresist parameters, wherein the one or more photoresist parameters characterize behavior of photoresist when the photoresist undergoes processing steps in the photolithography cluster, wherein the simulated diffraction signal was generated using one or more values of one or more profile parameters, and wherein the one or more values of the one or more profile parameters used to generate the simulated diffraction signal were derived from the one or more values of the one or more photoresist parameters associated with the simulated diffraction signal;
- c) if the measured diffraction signal and the simulated diffraction signal match, then determining one or more values of one or more photoresist parameters used in the photolithography cluster to be the one or more values of the one or more photoresist parameters associated with the matching simulated diffraction signal; and
- d) adjusting one or more process parameters or equipment settings of the photolithography cluster based on the one or more values of the one or more photoresist parameters determined c).

12. The computer-readable storage medium of claim 11, further comprising instructions for:
- if the measured diffraction signal and the simulated diffraction signal compared in b) do not match, comparing the measured diffraction signal to another simulated diffraction signal associated with one or more values of one or more photoresist parameters that are different than the one or more values of the one or more photoresist parameters of the simulated diffraction signal that did not match the measured diffraction signal.

13. The computer-readable storage medium of claim 12, wherein the simulated diffraction signal and the another simulated diffraction signal are stored in a library having a plurality of simulated diffraction signals and a plurality of values of one or more photoresist parameters associated with the plurality of simulated diffraction signals.

14. The computer-readable storage medium of claim 12, wherein the another simulated diffraction signal was generated after the measured diffraction signal and the simulated diffraction signal compared in b) are determined not to match.

15. The computer-readable storage medium of claim 11, wherein the one or more photoresist parameters comprise change of inhibitor concentration, surface inhibition, diffusion during the photoresist baking process, development rate parameters, labile absorptivity, non-labile absorptivity, and/or intrinsic sensitivity of the photoresist.

16. The computer-readable storage medium of claim 11, further comprising:
- adjusting one or more process parameters or equipment settings of a fabrication cluster based on the one or more values of the one or more photoresist parameters determined in c).

17. The computer-readable storage medium of claim 16, wherein the fabrication cluster processes wafers prior to the photolithography cluster.

18. The computer-readable storage medium of claim 16, wherein the fabrication cluster processes wafers subsequent to the photolithography cluster.

19. A system to control a photolithography cluster using optical metrology, the system comprising:
- a photolithography cluster configured to perform a photolithographic process to fabricate a structure on a wafer;
- an optical metrology system comprising:
  - a beam source and detector configured to measure a diffraction signal off the structure;
  - a processor connected to the beam source and detector, wherein the processor is configured to compare the measured diffraction signal to a simulated diffraction signal, wherein the simulated diffraction signal is associated with one or more values of one or more photoresist parameters, wherein the one or more photoresist parameters characterize behavior of photoresist when the photoresist undergoes processing steps in the photolithography cluster, wherein the simulated diffraction signal was generated using one or more values of one or more profile parameters, and wherein the one or more values of the one or more profile parameters used to generate the simulated diffraction signal were derived from the one or more values of the one or more photoresist parameters associated with the simulated diffraction signal; and
- a metrology processor coupled to the optical metrology system and the photolithography cluster, wherein the metrology processor is configured to adjust one or more process parameters or equipment settings of the photolithography cluster based on the one or more values of the one or more photoresist parameters determined by the processor of the optical metrology system.

20. The system of claim 19, further comprising:
- a library having a plurality of simulated diffraction signals and a plurality of values of one or more photoresist parameters associated with the plurality of simulated diffraction signals.

21. The system of claim 19, wherein the one or more photoresist parameters comprise change of inhibitor concentration, surface inhibition, diffusion during the photoresist baking process, development rate parameters, labile absorptivity, non-labile absorptivity, and/or intrinsic sensitivity of the photoresist.

22. The system of claim 19, further comprising:
a fabrication cluster connected to the metrology processor, wherein the metrology processor is configured to adjust one or more process parameters or equipment settings of the fabrication cluster based on the determined one or more values of the one or more photoresist parameters.

23. The system of claim 22, wherein the fabrication cluster processes wafers prior to the photolithography cluster.

24. The system of claim 22, wherein the fabrication cluster processes wafers subsequent to the photolithography cluster.

* * * * *